US010544674B2

(12) United States Patent
Bouldin et al.

(10) Patent No.: US 10,544,674 B2
(45) Date of Patent: Jan. 28, 2020

(54) MULTIPHASE FLOW METER WITH TUNING FORK

(71) Applicant: Saudi Arabian Oil Company, Dhahran (SA)

(72) Inventors: Brett W. Bouldin, Dhahran (SA); Robert John Turner, Dhahran (SA); Frode Hveding, Dhahran (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 149 days.

(21) Appl. No.: 15/684,660

(22) Filed: Aug. 23, 2017

(65) Prior Publication Data

US 2019/0063216 A1 Feb. 28, 2019

(51) Int. Cl.
*E21B 49/08* (2006.01)
*E21B 49/00* (2006.01)
(Continued)

(52) U.S. Cl.
CPC ............. *E21B 49/08* (2013.01); *E21B 41/00* (2013.01); *E21B 47/06* (2013.01); *E21B 47/065* (2013.01);
(Continued)

(58) Field of Classification Search
CPC .......... E21B 49/08; E21B 47/06; E21B 47/00; E21B 41/00; E21B 47/065; E21B 43/14; E21B 47/12; E21B 2049/08; G01N 2009/006; G01N 9/002; G01F 1/44; G01F 1/88; G01F 1/84; G01F 1/74
See application file for complete search history.

(56) References Cited

U.S. PATENT DOCUMENTS 4,526,480 A * 7/1985 Ward .................... G01N 9/002
374/117
6,831,470 B2 12/2004 Xie et al.
(Continued)

FOREIGN PATENT DOCUMENTS

| WO | WO2001022041 A1 | 3/2001 |
| WO | 2011053714 | 5/2011 |
| WO | WO2013005091 A2 | 1/2013 |

OTHER PUBLICATIONS

International Search Report and Written Opinion issued in International Application No. PCT/US2018/047254 dated Oct. 17, 2018, 23 pages.
(Continued)

*Primary Examiner* — Michael R Wills, III
(74) *Attorney, Agent, or Firm* — Fish & Richardson P.C.

(57) ABSTRACT

A flow meter includes a cylindrical tubing configured to be positioned in a wellbore, the cylindrical tubing including a flow mixer configured to produce a turbulent fluid flow of a multiphase fluid in the wellbore. The flow meter includes a tuning fork disposed in the cylindrical tubing separate from the flow mixer, the tuning fork configured to contact the turbulent fluid flow of the multiphase fluid and vibrate at a vibration frequency in response to contact with the turbulent fluid flow, and a controller to determine a fluid density measurement of the multiphase fluid based at least in part on the vibration frequency of the tuning fork.

21 Claims, 5 Drawing Sheets

(51) Int. Cl.
*E21B 47/06* (2012.01)
*G01F 1/44* (2006.01)
*G01F 1/74* (2006.01)
*G01F 1/84* (2006.01)
*E21B 41/00* (2006.01)
*E21B 43/14* (2006.01)
*E21B 47/12* (2012.01)

(52) U.S. Cl.
CPC ............... *G01F 1/44* (2013.01); *G01F 1/74* (2013.01); *G01F 1/84* (2013.01); *E21B 43/14* (2013.01); *E21B 47/12* (2013.01); *E21B 2049/085* (2013.01)

(56) References Cited

U.S. PATENT DOCUMENTS

| | | | |
|---|---|---|---|
| 6,938,470 B2 | 9/2005 | DiFoggio et al. | |
| 6,993,979 B2 | 2/2006 | Segeral | |
| 7,162,918 B2 | 1/2007 | DiFoggio et al. | |
| 7,317,989 B2 * | 1/2008 | DiFoggio | E21B 47/10 166/264 |
| 7,908,930 B2 | 3/2011 | Xie et al. | |
| 8,521,436 B2 * | 8/2013 | Agar | G01F 1/44 702/12 |
| 9,116,105 B2 | 8/2015 | Veneruso et al. | |
| 9,121,237 B2 * | 9/2015 | Kumar | C23C 30/005 |
| 9,441,997 B2 | 9/2016 | Downie et al. | |
| 2002/0178805 A1 | 12/2002 | DiFoggio et al. | |
| 2002/0178837 A1 | 12/2002 | Brandt | |
| 2009/0058226 A1 | 3/2009 | Furuhata et al. | |
| 2013/0255370 A1 | 10/2013 | Roux et al. | |
| 2014/0136125 A1 | 5/2014 | Agar et al. | |

OTHER PUBLICATIONS

Raza et al., "Liquid Density Measurement using Tuning Fork," International Journal of Current Engineering and Technology, vol. 5, No. 1, Feb. 2015, 4 pages.

Heinisch et al., "Resonant Steel Tuning Forks for Precise Inline Viscosity and Mass Density Measurements in Harsh Environments," Proceedia Engineering 87, Published in 2014, 4 pages.

Zheng et al., "Design and Theoretical Analysis of a Resonant Sensor for Liquid Density Measurement," ISSN 1424-8220, published in 2012, 12 pages.

Gonzalez et al., "Downhole Viscosity Measurement Platform using Tuning Fork Oscillators," Copyright 2015, 4 pages.

* cited by examiner

MULTIPHASE FLOW METER WITH TUNING FORK

TECHNICAL FIELD

This disclosure relates to flow meters, for example, for well tools in downhole wellbores or surface flow meters.

BACKGROUND

In-well flow meters are used in well systems, such as hydrocarbon-bearing wells, to measure fluid characteristics of a well fluid, such as flow rate and fluid type to determine pressure, temperature, and viscosity, among others. An in-well flow meter to measure fluid density includes several sensors and uses several math algorithms to interpret complex fluid flows of a fluid in a well system. An example of such an in-flow well meter is a venturi meter coupled with a nuclear source and detector to measure fluid density. Sometimes, a flow meter is placed on or is integral to a well tool disposed in a wellbore to measure fluid characteristics of the wellbore fluid during well drilling or production operations.

SUMMARY

This disclosure describes multiphase flow meters, for example, flow meters with a tuning fork disposed downhole in a wellbore or at the surface.

In some aspects, a flow meter includes a cylindrical tubing to be positioned in a wellbore, the cylindrical tubing including a flow mixer to produce a turbulent fluid flow of a multiphase fluid in the wellbore. The flow meter further includes a tuning fork disposed in the cylindrical tubing separate from the flow mixer, the tuning fork configured to contact the turbulent fluid flow of the multiphase fluid and vibrate at a vibration frequency in response to contact with the turbulent fluid flow, and a controller to determine a fluid density measurement of the multiphase fluid based at least in part on the vibration frequency of the tuning fork.

This, and other aspects, can include one or more of the following features. The tuning fork can be disposed in the cylindrical tubing downstream of the flow mixer. The flow mixer can include a venturi. The tuning fork can include two prongs disposed about a radial center of the cylindrical tubing. The tuning fork can include a hydrophobic coating on outer surfaces of the tuning fork. The tuning fork can be passive, and the passive tuning fork can vibrate in response to contact with the turbulent multiphase fluid flow at the vibration frequency depending on a density of the multiphase fluid. The flow meter can include a diaphragm connected to a base of the tuning fork, and at least one of a fiber optic cable or an electrical vibration sensor connected to the diaphragm to receive the vibration frequency through the diaphragm. The flow meter can include an electrical or mechanical source connected to the tuning fork to vibrate the tuning fork at a first active frequency, where the tuning fork can be configured to vibrate at the vibration frequency different from the first active frequency in response to contact with the turbulent multiphase fluid flow, the vibration frequency depending on a density of the multiphase fluid flow. The flow meter can include a diaphragm connected to a base of the tuning fork, and an electrical vibration sensor connected to the diaphragm to receive the vibration frequency through the diaphragm. The electrical vibration sensor can include a piezoelectric sensor. The multiphase fluid can include a two-phase fluid including water and hydrocarbons.

Certain aspects of the disclosure encompass a method including mixing, with a flow mixer in a cylindrical tubing, a multiphase fluid flowing through the cylindrical tubing disposed in a wellbore to produce a turbulent fluid flow of the multiphase fluid, vibrating a tuning fork in contact with the turbulent flow of the multiphase fluid at a vibration frequency, the tuning fork disposed separate from and downstream of the flow mixer, and determining, with a controller, a fluid characteristic of the multiphase fluid based at least in part on the vibration frequency.

This, and other aspects, can include one or more of the following features. The tuning fork can be passive, and vibrating the tuning fork at the vibration frequency can include vibrating the passive tuning fork at the vibration frequency depending on a density of the turbulent fluid flow of the multiphase fluid contacting the tuning fork. The method can include transferring, with a diaphragm, the vibration frequency from the tuning fork exposed to the multiphase fluid flow to at least one of a fiber optic cable or an electrical vibration sensor. Vibrating a tuning fork at a vibration frequency can include actively vibrating, with an electrical or mechanical resonator, the tuning fork at a first vibration frequency and vibrating, at a second vibration frequency different from the first frequency, the tuning fork in response to contact with the turbulent fluid flow of the multiphase fluid, the second frequency depending on a density of the multiphase fluid flow. The method can include transferring, with a diaphragm, the second frequency from the tuning fork exposed to the multiphase fluid flow to an electrical vibration sensor. Transferring the second frequency to an electrical vibration sensor can include transferring the second frequency to a piezoelectric sensor. Mixing, with a flow mixer in a cylindrical tubing, a multiphase fluid flowing through the cylindrical tubing disposed in a wellbore can include flowing the multiphase fluid through a venturi section of the cylindrical tubing to produce the turbulent fluid flow of the multiphase fluid. Determining a fluid characteristic of the multiphase fluid based at least in part on the vibration frequency can include determining a density of the multiphase fluid flow based at least in part on the vibration frequency of the tuning fork. The method can include measuring, with at least one of a temperature sensor or a pressure sensor, a temperature of the multiphase fluid flow, and determining a density of the multiphase fluid flow can include solving for the density of the multiphase fluid flow based at least in part on the vibration frequency of the tuning fork and the measured temperature of the multiphase fluid flow.

Certain aspects of the disclosure encompass a method for determining density of a two-phase wellbore fluid. The method includes mixing, with a flow mixer of a cylindrical tubing, a two-phase fluid flowing through the cylindrical tubing disposed in a wellbore to produce a turbulent fluid flow of the two-phase fluid, vibrating a passive tuning fork in contact with the turbulent fluid flow of the two-phase fluid at a vibration frequency based on a density of the two-phase fluid, the tuning fork disposed separate from and downstream of the flow mixer, and determining, with a controller, the density of the two-phase fluid based at least in part on the vibration frequency of the tuning fork.

The details of one or more implementations of the subject matter described in this disclosure are set forth in the accompanying drawings and the description later. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure describes a flow meter that measures characteristics of a multiphase fluid in a well, for example, to determine an average density (or other characteristics) of the multiphase fluid. The flow meter is configured to be disposed on and carried by a production string, drill string, or other well string in a wellbore, or disposed in a production pipeline or well header downstream of the wellhead. The multiphase fluid flows through a flow mixer of the flow meter well tool that produces a turbulent, well-mixed flow of the multiphase fluid. The multiphase fluid can include, for example, a fluid including water, oil, gas, or a combination of these. In some examples, the multiphase fluid is a two-phase fluid including water and oil, where the oil includes hydrocarbons. A tuning fork positioned in the turbulent flow vibrates in response to contact with the turbulent flow of the multiphase fluid. A resulting vibration frequency of the tuning fork is based at least in part on the density of the multiphase fluid flowing through the flow meter well tool, and the resulting vibration frequency can be measured and used to calculate the average density of the multiphase fluid. This disclosure also describes determining the fluid density of the multiphase fluid, for example, using the tuning fork of the flow meter well tool.

The present disclosure describes tuning forks disposed separate from a flow mixer, or venturi, and exposed to turbulent, well-mixed multiphase fluid flow to vibrate at a frequency dependent on an average density of the multiphase fluid. In some implementations, the tuning fork is passive, in that the tuning fork vibrates in response to contact with the turbulent multiphase fluid flow, and is not actively vibrated, for example, by a mechanical or electrical source. A flow meter well tool with a flow mixer and a tuning fork downstream of the flow mixer offers an accurate reading of the average density of a multiphase fluid, while also providing long term and stable operation and measurement.

Figure 1A:
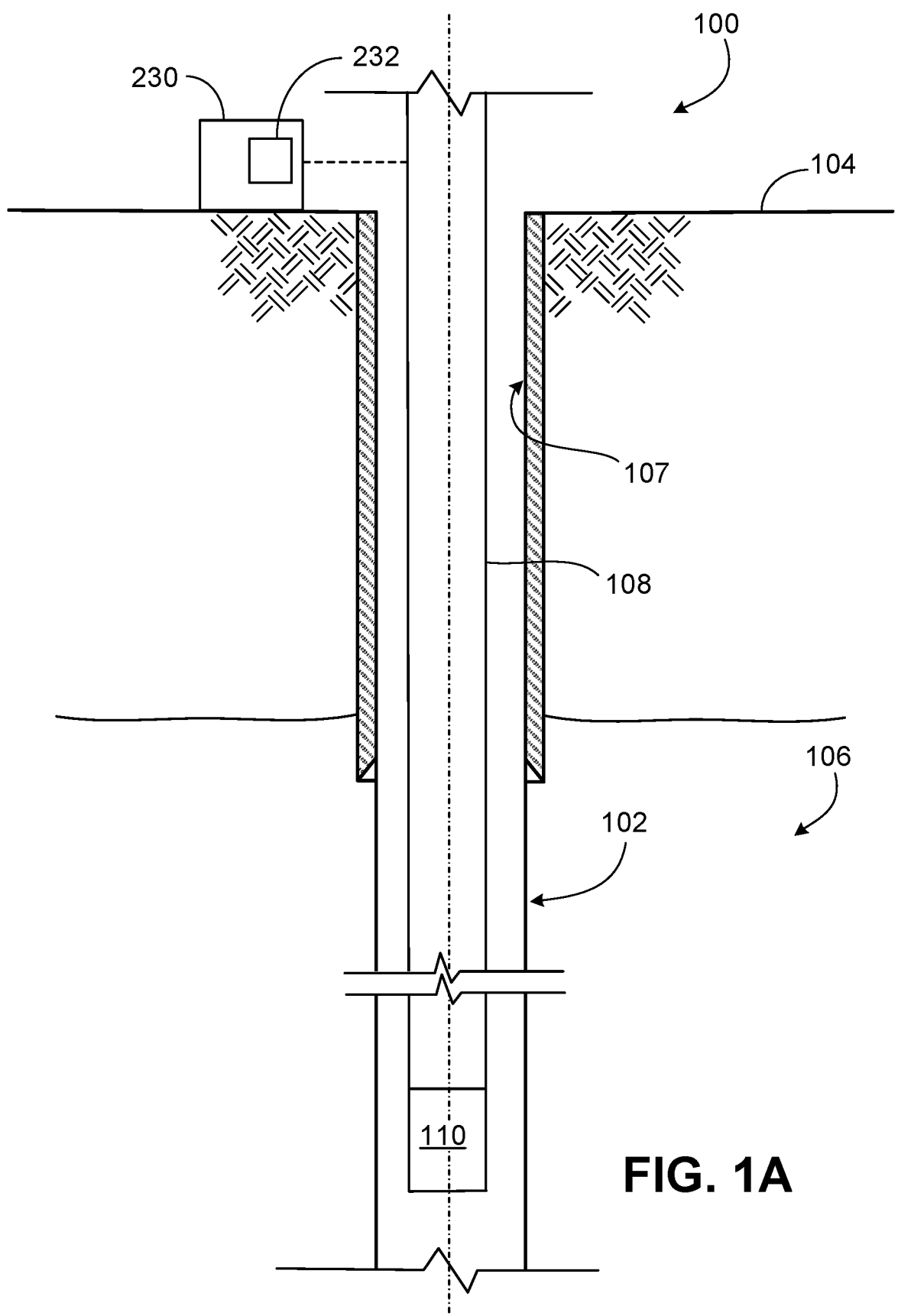
FIGS. 1A-1C are schematic partial cross-sectional views of example well systems.
Figure 1B:
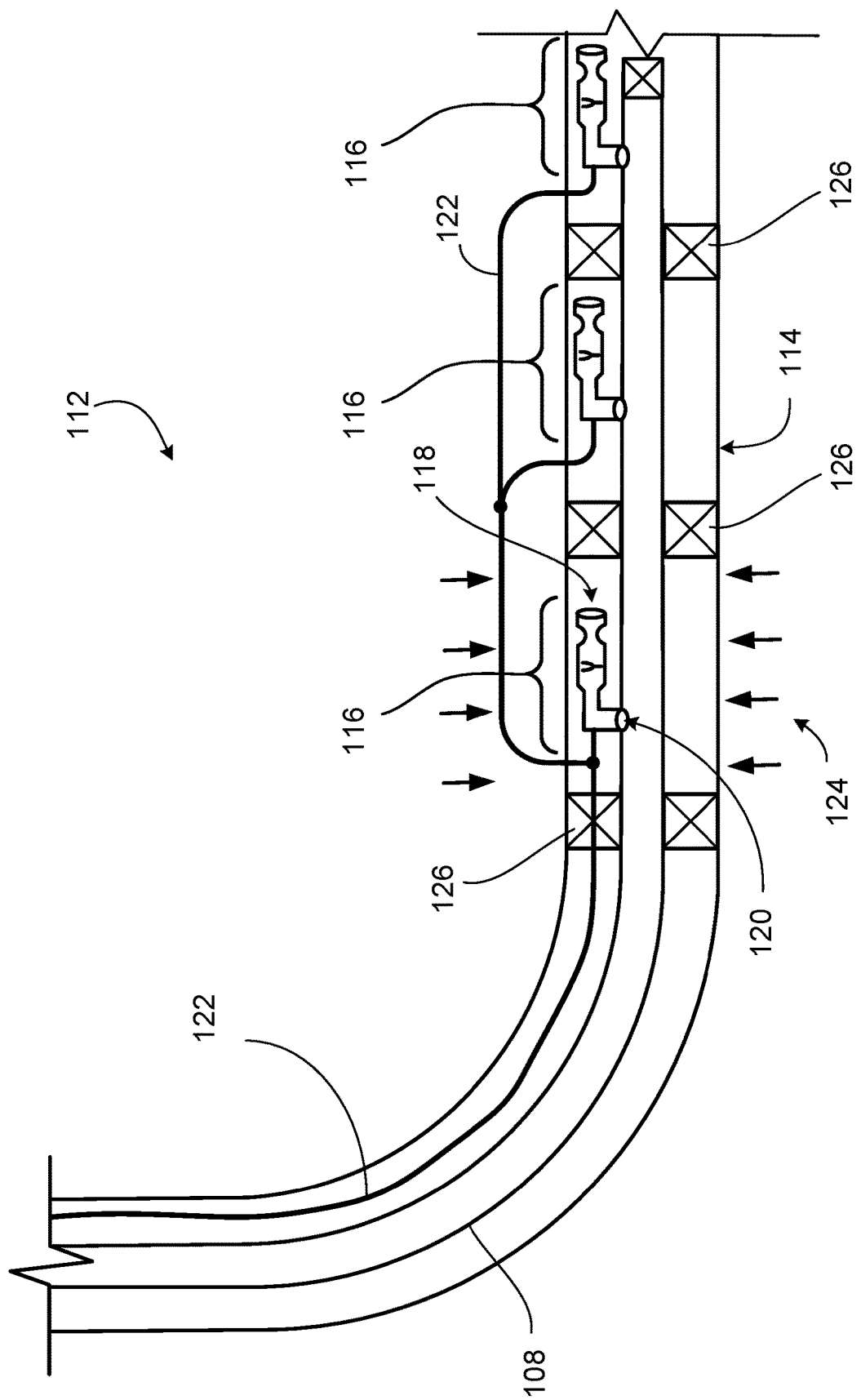
Figure 1C:
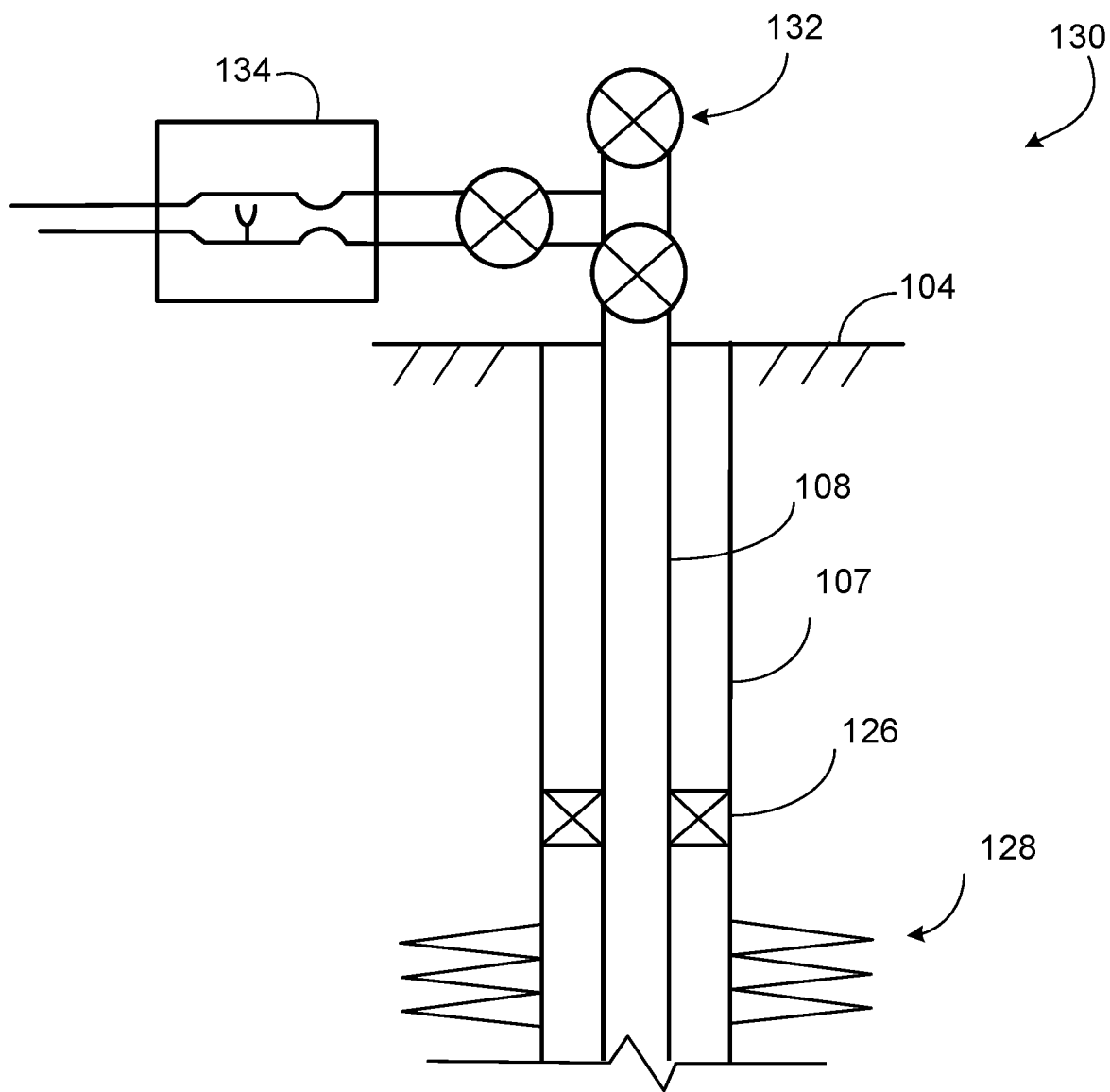

FIG. 1A is a schematic partial cross-sectional view of an example well system 100 that includes a substantially cylindrical wellbore 102 extending from a surface 104 downward into the Earth into one or more subterranean zones of interest 106 (one shown). The well system 100 includes a vertical well, with the wellbore 102 extending substantially vertically from the surface 104 to the subterranean zone 106. The concepts described here, however, are applicable to many other different configurations of wells, including horizontal, slanted, or otherwise deviated wells. In some implementations, the well system 100 includes a liner or casing 107 defined by lengths of tubing lining a portion of the wellbore 102 extending from the surface 104 into the Earth. A well string 108 is shown as having been lowered from the surface 104 into the wellbore 102. In some instances, the well string 108 is a series of jointed lengths of tubing coupled together end-to-end or a continuous (that is, not jointed) coiled tubing. The well string 108 can make up a production string, drill string, or other well string used during the lifetime of a well system. In the example well system 100 of FIG. 1A, the well string 108 includes a flow meter well tool 110. The flow meter well tool 110 is shown in FIG. 1A at a bottommost, downhole end of the well string 108. However, the location of the flow meter well tool 110 can vary on the well string 108, and more than one flow meter well tool 110 can be distributed along the well string 108. In some implementations, a flow meter well tool can be positioned at an intermediate location between a tophole end and a bottomhole end of the well string 108. For example, FIG. 1B is a schematic partial cross-sectional view of an example well system 112, similar to the well system 100 of FIG. 1A, except the well system 112 includes a horizontal wellbore 114 and includes multiple flow meters 116 (for example, three flow meters 116) distributed along a longitudinal length of the well string 108. The flow meters 116 can include inlets 118 and outlets 120, and can be connected by an electrical umbilical 122, as explained in more detail later. The flow meters 116, inlets 118, outlets 120, and umbilical 122 are shown schematically in FIG. 1B. Arrows indicated by reference number 124 show compartment inflow, such as formation fluid flow from the formation into the wellbore 114 annulus. The well system 112 of FIG. 1B also includes packer elements 126, for example, that can separate the wellbore into multiple production zones, and can be used to plug, seal, or otherwise control wellbore fluid flow in respective zones, such as formation fluid entering the wellbore from perforations. In some implementations, a flow meter well tool can be positioned outside of the wellbore 102, for example, in a downstream production pipeline or other downstream fluid passageway. For example, FIG. 1C shows a schematic partial cross-sectional view of an example well system 130, similar to the well system 100 of FIG. 1A, except the well system 130 includes a wellhead 132 with a surface flow meter 134 similar to flow meter 110 of FIG. 1A, and perforations 128 in the casing 108 into the adjacent formation. In some implementations, the example well system 100, 112, or 130 includes a control system 230 communicably coupled to the flow meter well tool 110, 116, or 134. The control system 230 includes a controller 232, and is described in more detail later.

Figure 2:
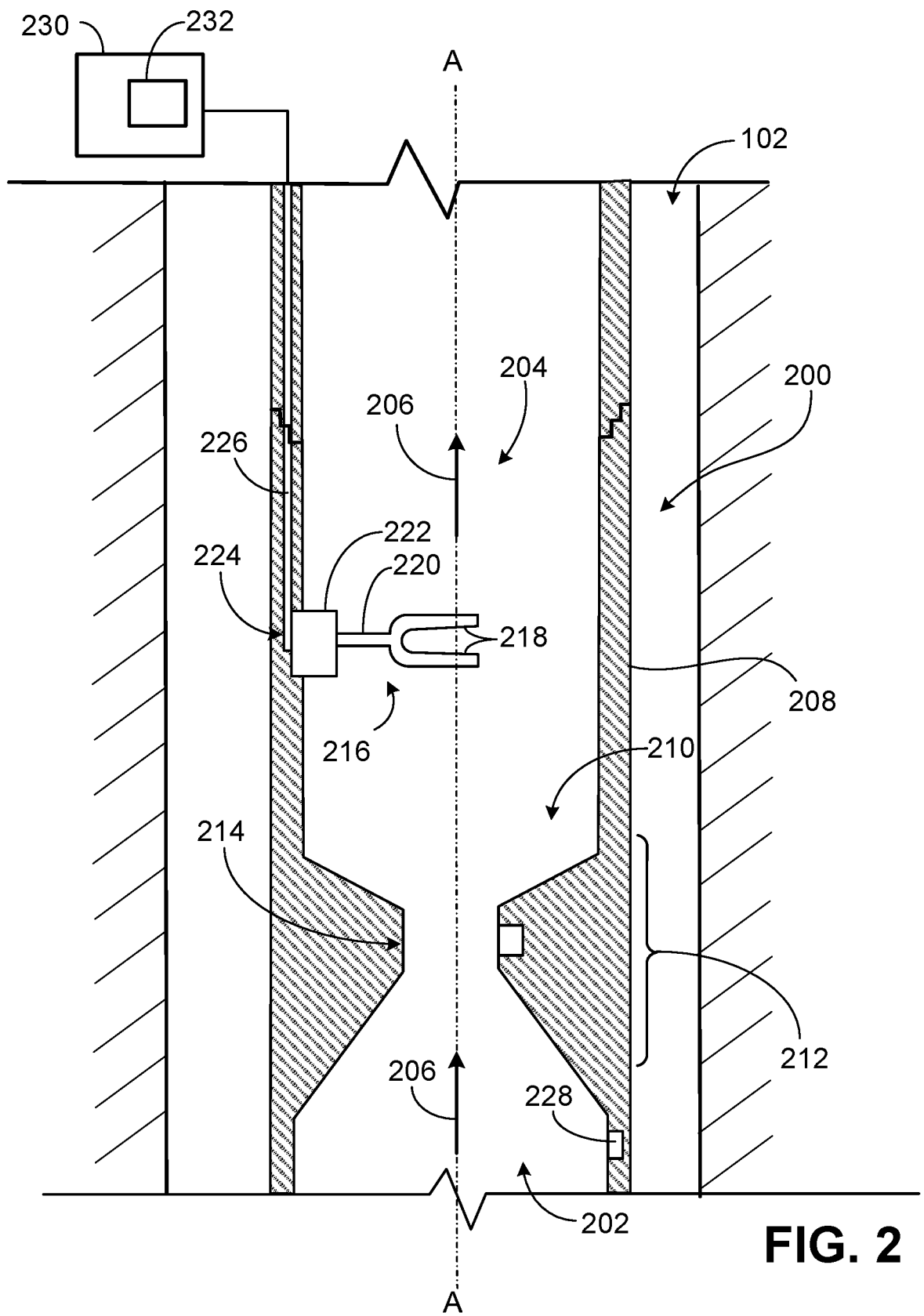
FIG. 2 is a schematic partial cross-sectional view of an example flow meter.

FIG. 2 is a cross-sectional side view of an example flow meter 200 that can be used in the flow meter well tool 110 of FIG. 1A. The example flow meter 200 is shown in FIG. 2 as positioned in wellbore 102. The example flow meter 200 receives at least a portion of the flow of multiphase fluid at an inlet 202, for example, from the wellbore 102 or from a downhole tubing connected to the inlet 202, and expels the fluid flow at an outlet 204 of the flow meter 200. In the example flow meter 200 of FIG. 2, the flow direction of the multiphase fluid, indicated by arrows 206, is in an uphole direction from inlet 202 to outlet 204. In the example flow meter 200 of FIG. 2, the uphole direction generally relates to a direction toward a well surface, for example, toward the surface 104 of the well system 100 of FIG. 1A. This uphole direction coincides with a downstream flow, where fluid flows from a downhole location in the wellbore 102, relative to the position of the flow meter 200, in the uphole direction toward the surface 104.

The flow meter 200 includes a substantially cylindrical tubing 208 to guide the multiphase fluid flow through the flow meter 200. A flow mixer 210 in the cylindrical tubing 208 agitates the multiphase fluid flow to create a turbulent flow downstream of the flow mixer 210. The flow mixer 210 is shown in FIG. 2 as including a venturi 212, for example, formed by the inner surface of the cylindrical tubing 208. A tuning fork 216, positioned in the cylindrical tubing separate from the flow mixer 210, contacts the turbulent flow of the multiphase fluid and can vibrate at a vibration frequency in response to contact with the turbulent flow. In some implementations, the multiphase flow upstream of the flow meter 200 includes laminar or stratified flow, where the multiphase fluid is not well mixed. The flow mixer 210 mixes the flow of the multiphase fluid to create a turbulent flow, where the multiphase fluid is well mixed. In the example flow meter 200 of FIG. 2, the flow mixer 210 includes the venturi 212, and the venturi 212 acts to agitate the flow by decreasing the tubing diameter at a throat 214 of the venturi 212, then returning the tubing to its original diameter. For example, laminar or stratified fluid flow can exist in the cylindrical tubing 208 when the diameter of the cylindrical tubing 208 is approximately one inch. A diameter of approximately 0.4 inches of the venturi throat 214 in the cylindrical tubing 208 can produce a turbulent fluid flow in the tubing 208 exiting the venturi 212. However, the diameter of the cylindrical tubing can vary. In some examples, the cross-sectional area at the venturi is substantially or exactly equal to 0.16*A, where A is the cross-sectional inlet area of the cylindrical tubing. The multiphase fluid is well mixed after exiting the venturi 212 because, as the pipe diameter widens downstream of the throat 214 of the venturi 212, the fluid is mixed in the turbulent flow following the venturi 212.

Although FIG. 2 shows the flow mixer 210 as including a venturi 212, the flow mixer can take a variety of forms to mix the multiphase fluid into a turbulent fluid flow. For example, the flow mixer 210 can include baffles extending radially inward from the inner walls of the tubing 208, an agitator, a static mixer, a vortex, a choke, visco jets, bluffs to create eddies, a combination of these features, or other fluid mixing structures integral to or connected to the cylindrical tubing 208 to create a well-mixed flow of the multiphase fluid downstream of the flow mixer 210.

The tuning fork is disposed in the cylindrical tubing 208 separate from the flow mixer 210 and within an area of the turbulent flow. In FIG. 2, the tuning fork 216 is positioned downstream of the venturi 212, for example, so that the tuning fork 216 is exposed to the turbulent flow of the multiphase fluid from the venturi 212. For example, in a cylindrical tubing 208 having a diameter of about one inch, the tuning fork 216 can be placed several inches downstream of the flow mixer 210. The separation between the tuning fork 216 and the flow mixer 210 can vary. For example, the tuning fork 216 can be separate from the flow mixer 210 a distance of a half inch, two inches, four inches, eight inches, one or more feet, or another distance. In some examples, the tuning fork 216 is separate from the flow mixer 210 a distance of four to ten exit diameters of the cylindrical tubing 208, but this distance can also be different. The fluid flow returns to laminar or stratified flow at a distance downstream of the venturi 212, and the location of the tuning fork 216 is chosen such that the tuning fork 216 is in the turbulent flow before the flow returns to laminar or stratified flow. The tuning fork 216 vibrates at a vibration frequency induced by the turbulent flow of the multiphase fluid. For example, fluid flowing past the tuning fork 216 causes the tuning fork 216 to vibrate, and the vibration frequency of the tuning fork 216 changes as a function of the fluid density of the multiphase fluid in contact with the tuning fork 216. The vibration frequency of the tuning fork 216 is based at least in part on the average density of the multiphase fluid contacting the tuning fork 216. The vibration frequency of the tuning fork 216 can be used to determine the average density of the multiphase fluid because the vibration frequency is dependent on the average density of the multiphase fluid.

In some implementations, the tuning fork 216 is passive. The passive tuning fork 216 vibrates in response to contact with the turbulent multiphase fluid flow, and does not require a source of energy to produce the vibration frequency based on the average fluid density. The flow of the well-mixed fluid contacting the tuning fork 216 vibrates the tuning fork 216, where the passive tuning fork 216 is not actively vibrated by an electrical or mechanical power source. In certain instances, the tuning fork 216 can be active, where an electrical or mechanical resonator actively vibrates the tuning fork 216 at a first vibration frequency, and the turbulent flow in contact with the tuning fork 216 disrupts, dampens, or otherwise affects the vibration of the tuning fork 216 to create a second vibration frequency different from the first frequency. This second vibration frequency depends on the density of the multiphase fluid flow and can be measured to determine the average density of the multiphase fluid. In some examples, the electrical or mechanical resonator can include one or more piezoelectric detectors.

The tuning fork 216 can include two prongs 218 disposed about a radial center of the cylindrical tubing 208. For example, the two prongs 218 are shown in FIG. 2 as disposed about a longitudinal centerline axis A-A of the flow meter 200. The two prongs 218 are substantially U-shaped, and connect at a primary stem 220. In some implementations, the tuning fork 216 includes a hydrophobic coating on exposed, outer surfaces of the tuning fork 216 (for example on the prongs 218, primary stem 220, or both) to reduce or prevent a film of fluid, such as water, from clinging to the surface and disrupting the vibration measurement. The tuning fork 216, more particularly the stem 220 of the tuning fork, connects to a diaphragm 222 that conveys the vibration frequency of the tuning fork 216 to a vibration sensor 224. The diaphragm 222 isolates the frequency signal from the environment (for example, fluid in the flow meter 200, wellbore 102, or both) and, in some instances, can amplify the frequency signal from the tuning fork 216 to the vibration sensor 224. The vibration sensor 224 is isolated from, or free from contact with, the multiphase fluid flow, for example, to ensure the frequency signal from the tuning fork 216 via the diaphragm 222 is not affected by the environment. The vibration sensor 224 can take a variety of forms, such as one or more fiber optic cables 226 (one shown in FIG. 2) or electrical umbilical (for example, electrical umbilical 122 of FIG. 1B), an electrical vibration sensor (for example, piezoelectric sensor or other), a combination of these, or another vibration sensor type. The vibration sensor 224 attaches to the diaphragm 222 to effect frequency transfer from the diaphragm 222 to the vibration sensor 224. For example, a fiber optic 226 can clamp to the diaphragm 222 at any point along a length of the fiber optic 226. In some examples, the type of vibration sensor 224 depends on whether the tuning fork 216 is operated as a passive tuning fork or an active tuning fork. For example, with an active tuning fork, the diaphragm 222 connects to an electrical sensor, such as a piezoelectric sensor or a spring loaded hammer, for example, that vibrates due to variations in the flow velocity and hits the tuning fork, or a fiber optic cable. In some examples, with a passive tuning fork, the diaphragm 222 connects to an electrical sensor, a fiber optic cable, or both. In some implementations, the flow meter can exclude the diaphragm 222, and the tuning fork 216 can attach directly to the vibration sensor 224 to transfer the vibration frequency from the tuning fork 216 to the vibration sensor 224.

In some implementations, the flow meter 200 connects to a control system 230 that receives the measurements from the vibration sensor 224, and any other sensor residing downhole in the wellbore 102 as part of the flow meter 200 or elsewhere. For example, the flow meter 200 of FIG. 2 can include pressure sensors 228 at the venturi 212 that can be communicably connected to the controller 232 to provide pressure data, temperature data, or both, of the multiphase flow through the venturi 212 to the controller 232. In some implementations, the control system 230 includes one or more processors and a computer-readable medium that stores computer instructions executable by the one or more processors. The control system 230 includes a controller 232 that interprets the received measurement data into outputs relating to fluid characteristics of the multiphase fluid, such as fluid density, temperature, pressure, viscosity, a combination of these characteristics, or other characteristics. The controller 232 can receive sensor input in substantially real time, for example, where the vibration frequency of the tuning fork 216 is transferred instantaneously to the vibration sensor 224, and the controller 232 receives the frequency input from the vibration sensor 224. The frequency at which the vibration frequency of the tuning fork 216 is measured can vary. For example, the vibration frequency can be measured one or more times per second. In some examples, the control system 230 includes a laser box that connects to, for example, couples to, the fiber optic cable 226. The laser box can pick up a vibration frequency and amplitude from one or more tuning forks of one or more flow meters. For example, the laser box can be located at the surface of the well system, can connect to the fiber optic cable 226, and due to its backscattering measuring principle, can sense the entire fiber optic cable 226 simultaneously to pick up the vibration frequency and amplitude at the location of one, some, or all of the tuning forks connected to the fiber optic cable.

The control system 230 can reside in the wellbore 102, at the surface 104 of the well, or located elsewhere. In some instances, the controller 232 is disposed locally to the flow meter 200 to receive measurements from the vibration sensor 224, any other sensor residing downhole, or a combination of these, whereas other components of the control system 230 are disposed above-ground, for example, at a well surface. The controller 232 can communicate with the control system 230 with a wired network, wireless network, or both.

The controller 232 can determine the average fluid density of the multiphase fluid based at least in part on the measured vibration frequency of the tuning fork 216. For example, the vibration sensor 224 connects to the controller 232 to provide the vibration frequency of the tuning fork 216, and other downhole sensors can connect to the controller to provide one or more of pressure, temperature, viscosity, or other downhole characteristics to the controller. In some implementations, the flow meter 200 can include a temperature sensor, pressure sensor (for example, at the venturi 212), or other sensor that provides data to the controller 232.

In some implementations with the tuning fork 216 placed downhole of the venturi 212, the venturi measures a mass flow rate of fluid from Equation 1:

$$\dot{m} = \rho V A \quad [\text{Eq. 1}]$$

where:
$\dot{m}$=Mass Flow Rate
$\rho$=Fluid Density
V=Fluid Velocity
A=Cross sectional flow area
If fluid density is known, then Equation 2 can be used to determine the volumetric flow rate of the fluid:

$$Q = C_D \frac{\pi d^2}{4} \frac{\varepsilon}{\sqrt{1-\beta^4}} \sqrt{\frac{2\Delta P}{\rho_{mix}}} \quad [\text{Eq. 2}]$$

where:
Q=Volumetric Flow Rate
$C_D$=Discharge coefficient
d=Throat diameter
$\beta$=d/D: Diameter ratio of throat to the upstream pipe D.
$\varepsilon$=Compressibility factor
$\Delta P$=Differential pressure across the Venturi
$\rho_{mix}$=Effective density of the two-phase mixture
The phase fractions of the fluid can then be determined using Equation 3:

$$\rho_{mix} = \alpha_1 \rho_1 + \alpha_2 \rho_2 \quad [\text{Eq. 3}]$$

where:
$\rho_{mix}$=Effective density of the two-phase mixture
$\alpha_1$=Water fraction
$\rho_1$=Water density
$\alpha_2$=Oil fraction
$\rho_2$=Oil density
A density measurement from a tuning fork can be found using Equation 4:

$$f = \frac{1.875^2}{2\pi l^2} \sqrt{\frac{EI}{\rho A}} \quad [\text{Eq. 4}]$$

where:
f=Frequency (Hz)
1.875 Smallest positive solution of cos(x)cos h(x)=−1
l=Length of fork prongs (m)
E=Young's Modulus of fork material (Pa)
I=Second moment of area of cross section (m$^4$)
$\rho$=Density of fork material (kg/m$^3$)
A=Cross sectional area of fork prongs (m$^2$)
Average density can be considered as effective density. For example, average density can be the density at time=t of a two phase fluid. Since each phase of the multi-phase fluid has its own density, the average density is somewhere between the two phases. The water fraction and the oil fraction (for example, $\alpha_1$ and $\alpha_2$ of Eq. 3) can affect the determination of average fluid density. The presence of fluid introduces damping and mass loading as the tuning fork oscillates. Equations 5 and 6 are example equations that factor damping and mass loading effects on a tuning fork in preparing the tuning fork for density sensor applications:

$$\gamma = \frac{1}{2} \frac{CS}{m_{vac}} \left(\frac{f_0}{f_{vac}}\right)^2 \sqrt{\frac{\rho \mu f_0}{\pi}} \quad [\text{Eq. 5}]$$

$$\left(\frac{f_{vac}}{f_0}\right)^2 = 1 + \beta \frac{\rho}{\rho_{LN}} + \frac{B}{\rho_{LN}} \frac{S}{V} \sqrt{\frac{\rho \mu}{\pi f_0}} \quad [\text{Eq. 6}]$$

where $f_0$ and $\gamma$ are the measured frequency and damping in a test fluid, and $f_{vac}$ and $m_{vac}$ are the frequency and mass in vacuum. The term $\rho_{LN}$ is the density of lithium niobate. After making measurements of a resonance peak in vacuum and in a test fluid of known viscosity and density, the unknown parameters $f_{vac}$, C, B, and $\beta$ can be obtained and the tuning fork can be used as a density sensor. To use the tuning fork as a density sensor, the density of lithium niobate in Equation 6 can be replaced with the fluid density (for example, hydrocarbon fluid density) in the flowline, and Equation 6 can be solved to determine fluid density, for example, for fluid in the flowline in real time, at certain time instants, or both. The tuning fork is prepared for density sensor applications, and the previous equations can be used to solve for average fluid density based at least in part on the frequency of the tuning fork in turbulent fluid flow of the multiphase fluid.

The vibration frequency can be averaged over time, and correlated to an average fluid density of the multiphase fluid. In some instances, the vibration frequency of the tuning fork 216 can be affected by changes in temperature, viscosity, pressure, or other fluid characteristics, so these characteristics can be measured by the sensors mentioned previously or extrapolated from indirect fluid characteristic measurements, and accounted for when the controller determines the average fluid density of the multiphase fluid.

In some implementations, the control system 230 logs data regarding the multiphase fluid characteristics in a database. The database can also store information regarding tested correlations between vibration frequency of a tuning fork and average density of the multiphase fluid. For example, the controller 232 can access the database to determine an average fluid density of the multiphase fluid based on a measured vibration frequency of the tuning fork 216. In some instances, the tested correlations between vibration frequency and average fluid density in the database can be correlated based on temperature, pressure, any other parameter of the observed multiphase fluid, or a combination of these parameters.

Figure 3:
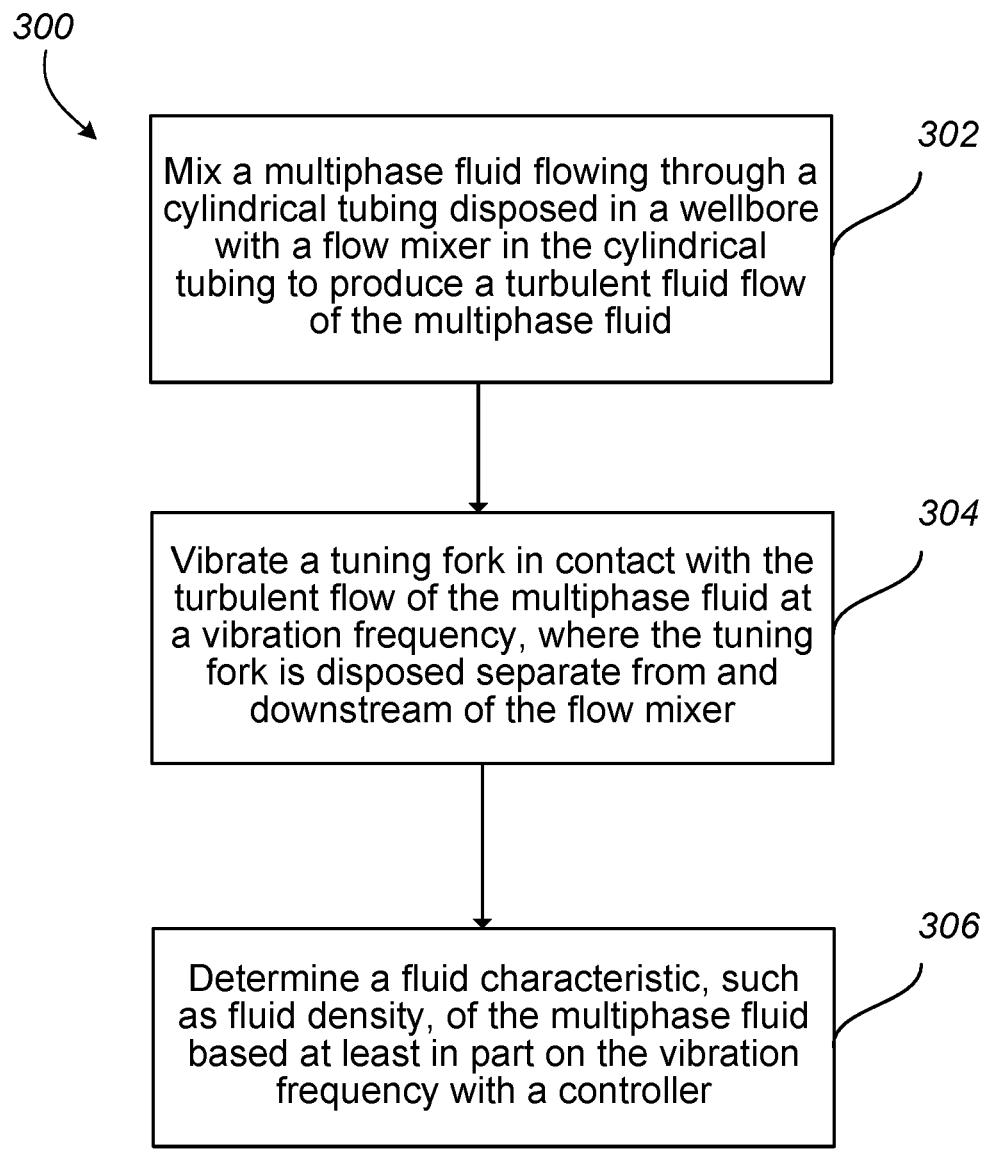
FIG. 3 is a flowchart describing a method for analyzing a fluid flow in a well.

FIG. 3 is a flowchart describing a method 300 of analyzing a multiphase fluid in a wellbore, for example, performed by the example flow meter 200 described earlier. At 302, a multiphase fluid flowing through a cylindrical tuning disposed in a wellbore is mixed by a flow mixer in the cylindrical tubing to produce a turbulent fluid flow of the multiphase fluid. At 304, a tuning fork in contact with the turbulent flow of the multiphase fluid vibrates at a vibration frequency, where the tuning fork is disposed separate from and downstream of the flow mixer. At 306, a fluid characteristic, such as fluid density, of the multiphase fluid is determined based at least in part on the vibration frequency using a controller.

A number of implementations have been described. Nevertheless, it will be understood that various modifications may be made without departing from the spirit and scope of the disclosure.

What is claimed is:

1. A flow meter comprising:
   a cylindrical tubing configured to be positioned in a wellbore, the cylindrical tubing comprising a flow mixer configured to produce a turbulent fluid flow of a multiphase fluid in the wellbore;
   a tuning fork disposed in the cylindrical tubing separate from the flow mixer, the tuning fork configured to contact the turbulent fluid flow of the multiphase fluid and vibrate at a vibration frequency in response to contact with the turbulent fluid flow; and
   a controller to determine a fluid density measurement of the multiphase fluid based at least in part on the vibration frequency of the tuning fork.

2. The flow meter of claim 1, wherein the tuning fork is disposed in the cylindrical tubing downstream of the flow mixer.

3. The flow meter of claim 1, wherein the flow mixer comprises a venturi.

4. The flow meter of claim 1, wherein the tuning fork comprises two prongs disposed about a radial center of the cylindrical tubing.

5. The flow meter of claim 1, wherein the tuning fork comprises a hydrophobic coating on outer surfaces of the tuning fork.

6. The flow meter of claim 1, further comprising an electrical or mechanical source connected to the tuning fork to vibrate the tuning fork at a first active frequency;
   wherein the tuning fork is configured to vibrate at the vibration frequency different from the first active frequency in response to contact with the turbulent multiphase fluid flow, the vibration frequency depending on a density of the multiphase fluid flow.

7. The flow meter of claim 6, further comprising a diaphragm connected to a base of the tuning fork; and
   an electrical vibration sensor connected to the diaphragm to receive the vibration frequency through the diaphragm.

8. The flow meter of claim 7, wherein the electrical vibration sensor comprises a piezoelectric sensor.

9. The flow meter of claim 1, wherein the multiphase fluid comprises a two-phase fluid comprising water and hydrocarbons.

10. A flow meter comprising:
    a cylindrical tubing configured to be positioned in a wellbore, the cylindrical tubing comprising a flow mixer configured to produce a turbulent fluid flow of a multiphase fluid in the wellbore;
    a tuning fork disposed in the cylindrical tubing separate from the flow mixer, the tuning fork configured to contact the turbulent fluid flow of the multiphase fluid and vibrate at a vibration frequency in response to contact with the turbulent fluid flow; and
    a controller to determine a fluid density measurement of the multiphase fluid based at least in part on the vibration frequency of the tuning fork, wherein the tuning fork is passive, and the passive tuning fork is configured to vibrate in response to contact with the turbulent multiphase fluid flow at the vibration frequency depending on a density of the multiphase fluid.

11. The flow meter of claim 10, further comprising:
    a diaphragm connected to a base of the tuning fork; and
    at least one of a fiber optic cable or an electrical vibration sensor connected to the diaphragm to receive the vibration frequency through the diaphragm.

12. A method, comprising:
    mixing, with a flow mixer in a cylindrical tubing, a multiphase fluid flowing through the cylindrical tubing disposed in a wellbore to produce a turbulent fluid flow of the multiphase fluid;
    vibrating a tuning fork in contact with the turbulent flow of the multiphase fluid at a vibration frequency, the tuning fork disposed separate from and downstream of the flow mixer; and
    determining, with a controller, a fluid characteristic of the multiphase fluid based at least in part on the vibration frequency.

13. The method of claim 12, wherein the tuning fork is passive, and wherein vibrating the tuning fork at the vibration frequency comprises vibrating the passive tuning fork at the vibration frequency depending on a density of the turbulent fluid flow of the multiphase fluid contacting the tuning fork.

14. The method of claim 13, further comprising transferring, with a diaphragm, the vibration frequency from the tuning fork exposed to the multiphase fluid flow to at least one of a fiber optic cable or an electrical vibration sensor.

15. The method of claim 12, wherein mixing, with the flow mixer in the cylindrical tubing, the multiphase fluid flowing through the cylindrical tubing disposed in the wellbore comprises flowing the multiphase fluid through a venturi section of the cylindrical tubing to produce the turbulent fluid flow of the multiphase fluid.

16. The method of claim 12, wherein determining a fluid characteristic of the multiphase fluid based at least in part on the vibration frequency comprises determining a density of the multiphase fluid flow based at least in part on the vibration frequency of the tuning fork.

17. The method of claim 16, further comprising measuring a temperature of the multiphase fluid flow with at least one of a temperature sensor or a pressure sensor; and
    wherein determining a density of the multiphase fluid flow comprises solving for the density of the multiphase fluid flow based at least in part on the vibration frequency of the tuning fork and the measured temperature of the multiphase fluid flow.

18. A method, comprising:
    mixing, with a flow mixer in a cylindrical tubing, a multiphase fluid flowing through the cylindrical tubing disposed in a wellbore to produce a turbulent fluid flow of the multiphase fluid;
    vibrating a tuning fork in contact with the turbulent flow of the multiphase fluid at a vibration frequency, the tuning fork disposed separate from and downstream of the flow mixer; and
    determining, with a controller, a fluid characteristic of the multiphase fluid based at least in part on the vibration frequency, wherein vibrating a tuning fork at a vibration frequency comprises actively vibrating, with an electrical or mechanical resonator, the tuning fork at a first vibration frequency and vibrating, at a second vibration frequency different from the first frequency, the tuning fork in response to contact with the turbulent fluid flow of the multiphase fluid, the second frequency depending on a density of the multiphase fluid flow.

19. The method of claim 18, further comprising transferring, with a diaphragm, the second frequency from the tuning fork exposed to the multiphase fluid flow to an electrical vibration sensor.

20. The method of claim 19, wherein transferring the second frequency to an electrical vibration sensor comprises transferring the second frequency to a piezoelectric sensor.

21. A method for determining density of a two-phase wellbore fluid, the method comprising:
    mixing, with a flow mixer of a cylindrical tubing, a two-phase wellbore fluid flowing through the cylindrical tubing disposed in a wellbore to produce a turbulent fluid flow of the two-phase wellbore fluid;
    vibrating a passive tuning fork in contact with the turbulent fluid flow of the two-phase wellbore fluid at a vibration frequency based on a density of the two-phase wellbore fluid, the tuning fork disposed separate from and downstream of the flow mixer; and
    determining, with a controller, the density of the two-phase wellbore fluid based at least in part on the vibration frequency of the tuning fork.

* * * * *